United States Patent
Nair et al.

(10) Patent No.: US 12,209,155 B2
(45) Date of Patent: Jan. 28, 2025

(54) MEMBRANE AND POLYMER FOR THE MANUFACTURE THEREOF

(71) Applicant: SOLVAY SPECIALTY POLYMERS USA, LLC, Alpharetta, GA (US)

(72) Inventors: Kamlesh Nair, Alpharetta, GA (US); Emanuele Di Nicolo', Gorla Minore (IT); Joel Pollino, Johns Creek, GA (US)

(73) Assignee: SOLVAY SPECIALTY POLYMERS USA, LLC, Alpharetta, GA (US)

( * ) Notice: Subject to any disclaimer, the term of this patent is extended or adjusted under 35 U.S.C. 154(b) by 423 days.

(21) Appl. No.: 17/628,254

(22) PCT Filed: Aug. 3, 2020

(86) PCT No.: PCT/EP2020/071807
§ 371 (c)(1),
(2) Date: Jan. 19, 2022

(87) PCT Pub. No.: WO2021/023711
PCT Pub. Date: Feb. 11, 2021

(65) Prior Publication Data
US 2022/0267497 A1    Aug. 25, 2022

Related U.S. Application Data

(60) Provisional application No. 62/883,269, filed on Aug. 6, 2019.

(30) Foreign Application Priority Data

Sep. 18, 2019 (EP) ..................................... 19197990

(51) Int. Cl.
| | | |
|---|---|---|
| C08F 283/00 | (2006.01) |
| A61M 1/16 | (2006.01) |
| B01D 61/24 | (2006.01) |
| B01D 69/02 | (2006.01) |
| B01D 69/04 | (2006.01) |
| B01D 69/08 | (2006.01) |
| B01D 71/44 | (2006.01) |
| B01D 71/68 | (2006.01) |
| B01D 71/80 | (2006.01) |

(52) U.S. Cl.
CPC ......... *C08F 283/00* (2013.01); *A61M 1/1621* (2014.02); *B01D 61/244* (2022.08); *B01D 69/02* (2013.01); *B01D 69/04* (2013.01); *B01D 69/08* (2013.01); *B01D 71/441* (2022.08); *B01D 71/68* (2013.01); *B01D 71/80* (2013.01); *B01D 2323/18* (2013.01); *B01D 2325/02* (2013.01)

(58) Field of Classification Search
CPC ................ A61M 1/1621; C08F 283/00; B01D 2323/18; B01D 2325/02; B01D 61/243; B01D 67/0006; B01D 69/02; B01D 69/04; B01D 69/08; B01D 71/68; B01D 71/80; B01D 61/244; B01D 71/44; B01D 71/441
USPC ......................................................... 210/646
See application file for complete search history.

(56) References Cited

U.S. PATENT DOCUMENTS

| | | |
|---|---|---|
| 8,596,467 B2 | 12/2013 | Krause et al. |
| 2011/0009799 A1 | 1/2011 | Mullick et al. |
| 2011/0240550 A1 | 10/2011 | Moore et al. |
| 2015/0008179 A1 | 1/2015 | Mullick et al. |

FOREIGN PATENT DOCUMENTS

| | | | |
|---|---|---|---|
| DE | 102014018481 A1 | 10/2015 | |
| EP | 0305787 A1 | 3/1989 | |
| EP | 2113298 A1 | 11/2009 | |
| EP | 2253369 A1 | 11/2010 | |
| EP | 2567750 A1 | 3/2013 | |
| EP | 3108955 A1 | 12/2016 | |
| EP | 3108956 A1 | 12/2016 | |
| WO | WO 2000/74877 A1 | 12/2000 | |
| WO | 2013034611 A1 | 3/2013 | |
| WO | WO-2015075178 A1 * | 5/2015 | ........... B01D 61/145 |

OTHER PUBLICATIONS

Porter M.C., "Pore size determination", in Handbook of Industrial Membrane Technology, 1990, p. 70-78—Noyes Publications.
Smolders, K. et al., "Terminology for membrane distillation", DESALINATION, 1989, vol. 72, pp. 249-262—Elsevier Science Publishers B.V., Amsterdam, NL.

* cited by examiner

*Primary Examiner* — Claire A Norris
(74) *Attorney, Agent, or Firm* — Beatrice C. Ortego

(57) ABSTRACT

The present invention relates to novel co-polymers and their use in the manufacture of porous membranes for haemodialysis application. In particular, such a co-polymer comprises a first segment comprising recurring units poly(aryl ether sulfone) [PAES recurring units], and a second segment comprising-recurring units poly(vinyl pyrrolidone) [PVP recurring units], wherein said first segment and said second segment are linked together via a group of formula —O-Ph-NH—C(=O)—C($CH_3$)$_2$—$CH_2$—.

19 Claims, No Drawings

MEMBRANE AND POLYMER FOR THE MANUFACTURE THEREOF

CROSS-REFERENCE TO RELATED PATENT APPLICATIONS

This application is a U.S. national stage entry under 35 U.S.C. § 371 of International Application No. PCT/EP2020/071807 filed Aug. 3, 2020, which claims priorities filed on 6 Aug. 2019 in the UNITED STATES with No. 62/883,269 and filed on 18 Sep. 2019 in EUROPE with Ser. No. 19/197,990.5, the whole content of these applications being incorporated herein by reference for all purposes.

TECHNICAL FIELD

The present invention relates to novel co-polymers and their use in the manufacture of porous membranes for haemodialysis application.

BACKGROUND ART

Porous membranes are discrete, thin interface that moderate the permeation of chemical species in contact with them. The key property of porous membranes is their ability to control the permeation rate of chemical species through the membrane itself. This feature is exploited in many different applications like separation applications (water and gas) or biomedical applications, such as drug delivery applications as well as haemodialysis, the extracorporeal process in which the blood is cleansed via removal of uremic retention products by a semipermeable membrane.

Polymeric membranes suitable for use as microfiltration and ultrafiltration typically control the permeation under a "sieve" mechanism, wherein the passage of liquid or gas is mainly governed by a convective flux.

Such polymeric membranes are mainly produced by phase inversion methods which allow to obtain items with very large fraction of voids (porosity).

For this purpose, a homogeneous polymeric solution (also referred to as "dope solution") containing a polymer, a suitable solvent and/or a co-solvent and, optionally, one or more additives, is typically casted into a film and then precipitated by contact with a non-solvent medium, in the so-called Non-Solvent Induced Phase Separation (NIPS) process. The non-solvent medium is usually water or a mixture of water and surfactants, alcohols and/or the solvent itself.

Precipitation can also be induced by decreasing the temperature of a polymeric solution, in the so-called Thermal Induced Phase Separation (TIPS) process.

Alternatively, in the so-called Vapour Induced Phase Separation (VIPS) process, precipitation can be induced by contacting a film obtained by casting with air having a very high water vapour content.

Still, precipitation may be induced by evaporation of the solvent from a film obtained by casting, in the so-called Evaporation Induced Phase Separation (EIPS) process. Typically in this process an organic solvent with low boiling point (such as tetrahydrofuran, acetone, methyl-ethyl-ketone and the like) is used in admixture with water (the so called "non-solvent") for the preparation of the polymer solution. The polymer solution is first extruded and then precipitates due to the evaporation of the volatile solvent and the enrichment of the non-solvent.

The above processes can be used in combination and/or in sequence to provide membranes having specific morphology and performances. For example, EIPS process can be combined with the VIPS process and NIPS process in order to complete the precipitation process.

Aromatic sulfones polymers are high performance polymers endowed with high mechanical strength and high thermal stability; they are used in a variety of industrial applications, including the manufacture of microfiltration membranes and ultrafiltration membranes, such as those used in the biomedical field. For example, micro-porous membranes used in the manufacture of haemodialysis devices can be obtained by spinning filaments from a dope solution (otherwise referred to as "spinning solution") comprising the polymer, a solvent, a pore-forming agent and a surface-modifying macromolecule, as disclosed, for example, in US 2011/009799 A (INTERFACE BIOLOGICS, INC.).

Even though the aromatic sulfone polymers currently used in the manufacture of microfiltration and ultrafiltration membranes have high mechanical strength and high thermal stability, there is the continuous need to obtain improved materials for the manufacture of haemodialysis membranes.

Membranes prepared from blends obtained by mixing together at least one hydrophobic first polymer (e.g., polyamide) and a hydrophilic second polymer (e.g., polyvinylpirrolidone), optionally with suitable additives have been widely disclosed in the art (for example in EP 0305787, EP 2113298 and U.S. Pat. No. 8,596,467).

However, membranes obtained using said blends are not suitable for use in haemodialysis application, because release of the hydrophilic polymer can occur, which leads to undesired healthy drawbacks for the patient, such as for example severe allergic reactions.

EP 2253369 (Gambro Lundia AB) discloses a permselective asymmetric membrane, said membrane comprising copolymer of vinylpyrrolidone and sulfobetaine comprising (meth)acrylic moieties.

WO 2013/034611 (Gambro Lundia AB) discloses a semipermeable asymmetric hollow fiber membrane, the material membrane being a graft copolymer of at least one hydrophobic polymer and at least one hydrophilic polymer. More in particular, the membrane is made of a graft copolymer of at least one polysulfone or polyether sulfone, preferably in an amount from 90 to 99 wt. % based on the total weight of the graft copolymer, and at least one polyvinyl pyrrolidone, preferably in an amount from 1 to 10 wt. %, based on the total weight of the graft copolymer.

The examples of this patent application showed a content of the chemically bound PVP in the final copolymer of about 2.0 wt. %. Without being bound by any theory, the Applicant is of the opinion that this low amount of PVP in the final copolymer is due to the mechanical process by which the final copolymer is obtained.

EP 3108955 (Pall Corporation) discloses porous membranes comprising an aromatic hydrophobic polymer and a wetting agent comprising a copolymer of formula A-B or A-B-A, wherein A is a hydrophilic segment comprising a polymerized monomer or mixture of monomers of formula $CH_2=C(R1)C(R2)$; and B is an aromatic hydrophobic polymeric segment, wherein B and A are linked through an amidoalkylthio group represented by the following formula: $—B—[NH—C(=O)—(CH_2)_a—S]-A-$.

The synthesis disclosed in this patent starts from the reaction of a diamine macromer (i.e., a difunctional starting compound) with sodium mercaptoacetate, to provide a macro-CTA (Chain Transfer Agent) terminated at both its chain ends with —SH group, which is then reacted with 1-vinylpyrrolid-2-one and azobis-isobutyronitrile (AIBN) to provide block copolymers of formula:

wherein said first segment and said second segment are linked together via a group of formula —O-Ph-NH—C(=O)—C(CH$_3$)$_2$—CH$_2$—.

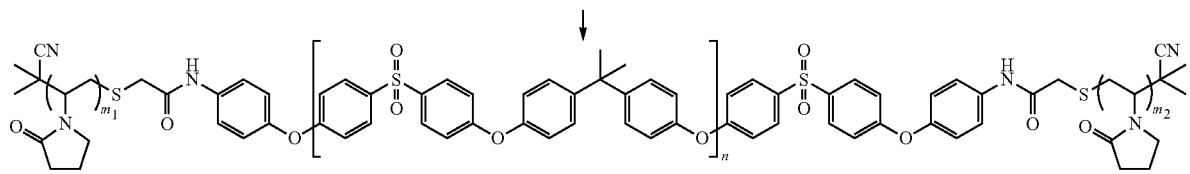

The aromatic hydrophobic polymer is selected from polysulfone (PSU), polyphenylene ether sulfone (PPES), polyethersulfones (PES), polycarbonate (PC), polyether ether ketone (PEEK), poly(phthalazinone ether sulfone ketone) (PPESK), polyphenyl sulfide (PPS), polyphenylene ether (PPE), polyphenylene oxide (PPO) and polyetherimide (PEI). The aromatic hydrophobic segment B can be selected from PSU, PPES, PES, PEEK, PPS, PPE, PPO or PEI, each terminated with one or preferably two amino-substituted moieties.

SUMMARY OF INVENTION

The Applicant perceived that the need still exists for membranes from which no release of the hydrophilic material occurs when said membrane is used in the biomedical field, more in particular for haemodialysis.

In particular, the Applicant noted that the synthesis disclosed in EP 3108955 in the name of Pall Corporation, cited above, requires the use of macromolecular chain transfer agent in order to obtain a block co-polymer having a pre-determined chemical structure. However, while chain-transfer agents have been used in free radical polymerizations, their use can lead to a reduction in the polymerization rate, and also lead to polymers characterized by a low molecular weight, e.g., with weight average molecular weight ($M_w$) from about 19 000 g/mol to about 30 000 g/mol (as determined by GPC).

The Applicant considered the copolymer disclosed in WO 2013/034611 (Gambro Lundia AB) but perceived that the low amount of PVP in the final copolymer (2.0 wt. % based on the total weight of the final copolymer, as shown in Example 1) was due do the fact that the copolymer was manufactured via a mechanical process.

Thus, the Applicant faced the problem of providing a co-polymer comprising at least one hydrophobic segment and at least one hydrophilic segment, which is obtainable via a chemical synthesis that is quick, easy to scale up to industrial plant and does not involve expensive reactants or starting materials.

Also, the Applicant faced the problem of providing a co-polymer having higher molecular weight compared to the co-polymers already disclosed in the art and comprising covalently bonded PVP, in a weight ratio well above 2% based on the total weight of the final co-polymer.

Thus, in a first aspect, the present invention relates to a co-polymer [co-polymer (P)] comprising:
  a first segment comprising, preferably consisting of, recurring units poly(aryl ether sulfone) [PAES recurring units], and
  a second segment comprising, preferably consisting of, recurring units poly(vinyl pyrrolidone) [PVP recurring units], Advantageously, said co-polymer (P) comprises more than 5 wt. % preferably more than 10 wt. % of PVP segment, based on the total weight of co-polymer (P).

Advantageously, said co-polymer (P) comprises at least 12 wt. %, even more preferably at least 15 wt. % of PVP segment, based on the total weight of co-polymer (P).

Advantageously, said co-polymer (P) is characterized by a weight average molecular weight ($M_w$) from 50000 g/mol to 2000000 g/mol (as determined by GPC).

In a second aspect, the present invention relates to a process for the synthesis of co-polymer (P) defined above, said process comprising the following steps:
  (I) providing a poly(aryl ether sulfone) polymer having two chain ends, wherein both chain ends comprise an amine group [polymer (PAES)NN];
  (II) reacting said polymer (PAES)NN with methacryloyl chloride thus providing a mixture [mixture (M-P1)] comprising mono-methacrylated PAES polymer [polymer (PAES)$_{NA}$] and di-methacrylated PAES polymer [polymer $_{NA}$(PAES)$_{NA}$];
  (III) reacting said mixture (M-P1) obtained in step (II) with vinyl pyrrolidone monomer, thus providing a mixture comprising polymer (P).

In a third aspect, the present invention relates to a composition [composition (C)] comprising:
  at least one polymer (P) as defined above, preferably in an amount from 0.01 to 30 wt. % based on the total weight of said composition (C),
  at least one PVP polymer, preferably in an amount from 1 to 10 wt. % based on the total weight of said composition (C);
  optionally, at least one poly(aryl ether sulfone) (PAES) polymer, preferably in an amount from 1 to 35 wt. % based on the total weight of said composition (C); and
  at least one solvent [medium (L)], preferably in an amount higher than 60 wt. % based on the total weight of said composition (C).

In a fourth aspect, the present invention relates to a membrane [membrane (Q)] comprising at least one porous layer [layer (L$_Q$)], said layer (L$_Q$) being obtained from composition (C) as defined above.

The Applicant surprisingly found that when a membrane is manufactured using co-polymer (P) according to the invention, said membrane can be used for haemodialysis application as the compatibility between the membrane and the blood is increased, while at the same time allergic reactions are avoided as PVP is not released in the human body.

In addition, the Applicant surprisingly found that using the co-polymer of the present invention, membranes having high hemo-compatibility are obtained, which means that no activating effect on the coagulation rate of the patient's blood was detected when the membranes of the invention were used.

Thus, in a further aspect, the present invention relates to a method for the extracorporeal treatment of a patient's body fluid, preferably of blood, said method comprising the use of at least one membrane (Q) according to the present invention.

DESCRIPTION OF EMBODIMENTS

For the purpose of the present description and of the following claims:
- the use of parentheses before and after symbols or numbers identifying compounds, chemical formulae or parts of formulae has the mere purpose of better distinguishing those symbols or numbers from the rest of the text and hence said parentheses can also be omitted;
- the term "membrane" is intended to indicate to a discrete, generally thin, interface that moderates the permeation of chemical species in contact with it, said membrane containing pores of finite dimensions, said pores having dimensions defined in the description below;
- when the membrane of the invention comprise the porous layer ($L_Q$) as the only layer, the term "membrane (Q)" is used to indicate said layer ($L_Q$) as the two coincide;
- the term "gravimetric porosity" is intended to denote the fraction of voids over the total volume of the porous membrane;
- the term "solvent" is used herein in its usual meaning, that is it indicates a substance capable of dissolving another substance (solute) to form an uniformly dispersed mixture at the molecular level. In the case of a polymeric solute, it is common practice to refer to a solution of the polymer in a solvent when the resulting mixture is transparent and no phase separation is visible in the system. Phase separation is taken to be the point, often referred to as "cloud point", at which the solution becomes turbid or cloudy due to the formation of polymer aggregates;
- "glass transition temperature ($T_g$)" is intended to indicate the temperature measured by differential scanning calorimetry (DSC) according to ASTM D3418 at 20° C./min as described in details in the examples;
- the term "porous" is intended to indicate that a membrane of the invention contains pores distributed throughout its thickness;
- the term "dense" associated to "film" or "layer" is intended to indicate that the film or the layer does not contain pores distributed throughout its thickness or, if pores are present, the gravimetric porosity is of less than 3%, more preferably less than 1%, based on the total volume of the film;
- the expression "as defined above" is intended to comprise all generic and specific or preferred definitions or embodiments referred to by that expression in preceding parts of the description;
- the term "process" and "method" are synonyms.

As mentioned above, co-polymer (P) according to the present invention comprises recurring units poly(aryl ether sulfones) [PAES recurring units].

Preferably, said PAES recurring units are selected in the group comprising, preferably consisting of, polyphenylsulfone (PPSU) recurring units, polyethersulfone (PES) recurring units, poly ether ether sulfone (PEES) recurring units and polysulfone (PSU) recurring units.

For the purpose of the present invention, poly(aryl ether sulfone) (PAES) is intended to indicate any polymer comprising at least 50 mol. % of recurring units ($R_{PAES}$) of formula (K):

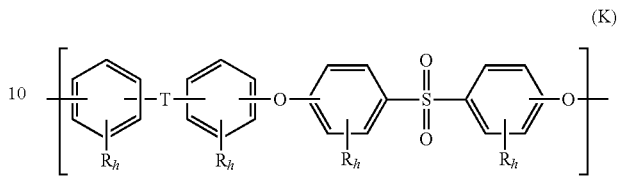

where
each R, equal to or different from each other, is selected from a halogen, an alkyl, an alkenyl, an alkynyl, an aryl, an ether, a thioether, a carboxylic acid, an ester, an amide, an imide, an alkali or alkaline earth metal sulfonate, an alkyl sulfonate, an alkali or alkaline earth metal phosphonate, an alkyl phosphonate, an amine, and a quaternary ammonium;
each h, equal to or different from each other, is an integer ranging from 0 to 4; and
T is selected from the group consisting of a bond, a sulfone group [—S(═O)$_2$—], and a group —C($R_j$)($R_k$)—, where $R_j$ and $R_k$, equal to or different from each other, are selected from a hydrogen, a halogen, an alkyl, an alkenyl, an alkynyl, an ether, a thioether, a carboxylic acid, an ester, an amide, an imide, an alkali or alkaline earth metal sulfonate, an alkyl sulfonate, an alkali or alkaline earth metal phosphonate, an alkyl phosphonate, an amine, and a quaternary ammonium. $R_j$ and $R_k$ are preferably methyl groups.

Preferably at least 60 mol. %, 70 mol. %, 80 mol. %, 90 mol. %, 95 mol. %, 99 mol. %, and most preferably all of recurring units in the PAES are recurring units ($R_{PAES}$).

In one embodiment, the PAES recurring units are polyphenylsulfone (PPSU) recurring units. As used herein, polyphenylsulfone (PPSU) recurring units is intended to indicate a polymer comprising more than 50 mol. % of recurring units of formula (K'-A):

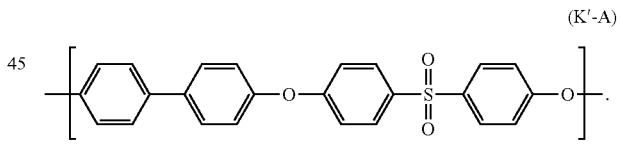

Preferably at least 60 mol. %, 70 mol. %, 80 mol. %, 90 mol. %, 95 mol. %, 99 mol. %, and most preferably all of the recurring units in the PPSU are recurring units of formula (K'-A).

In some embodiments, the PAES recurring units are polyethersulfone (PES) recurring units. As used herein, polyethersulfone (PES) recurring units is intended to indicate any polymer comprising at least 50 mol. % of recurring units of formula (K'-B):

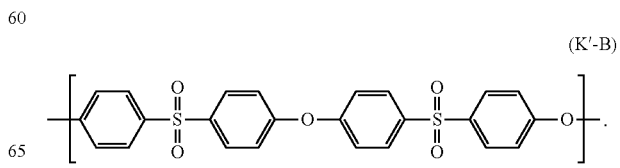

Preferably at least 60 mol. %, 70 mol. %, 80 mol. %, 90 mol. %, 95 mol. %, 99 mol. %, and most preferably all of the recurring units in the PES are recurring units of formula (K'-B).

In some embodiments, the PAES recurring units are polysulfone (PSU) recurring units. As used herein, polysulfone (PSU) recurring units is intended to indicate polymer comprising at least 50 mol. % of recurring units of formula (K'-C):

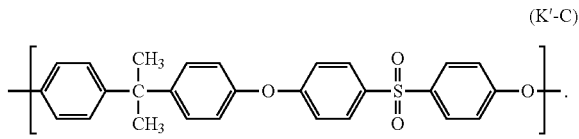

Preferably at least 60 mol. %, 70 mol. %, 80 mol. %, 90 mol. %, 95 mol. %, 99 mol. %, and most preferably all of the recurring units in the PSU are recurring units of formula (K'-C).

According to a preferred embodiment, the PAES recurring units are poly(ether ether sulfone) (PEES) recurring units. As used herein, poly(ether ether sulfone) (PEES) recurring units is intended to indicate polymer comprising at least 50 mol. % of recurring units of formula (K'-D):

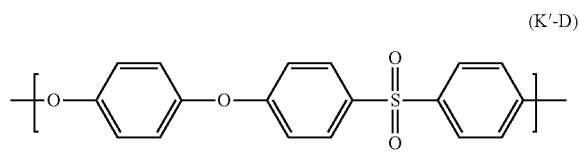

Preferably at least 60 mol. %, 70 mol. %, 80 mol. %, 90 mol. %, 95 mol. %, 99 mol. %, and most preferably all of the recurring units in the PSU are recurring units of formula (K'-D).

In addition to recurring unit of formula (K'-D), said PEES polymer con further comprise recurring units of formula (K'-db):

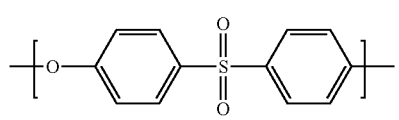

Excellent results have been obtained when the PAES recurring units where PSU recurring units or PEES recurring units.

As mentioned above, co-polymer (P) according to the present invention comprises recurring units poly(vinyl pyrrolidone) [PVP recurring units].

Said PVP recurring units preferably comply with the following formula (I):

wherein o is an integer higher than 1.

Advantageously, said co-polymer (P) comprise one segment comprising said PAES recurring units and one segment comprising said PVP recurring units, linked together via the group of formula —O-Ph-NH—C(=O)—C(CH$_3$)$_2$—CH$_2$—.

Preferably, co-polymer (P) complies with the following formula:

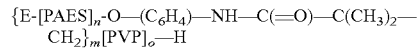

wherein

[PAES] indicates PAES recurring units as defined above, more preferably PEES recurring units;

[PVP] indicates PVP recurring units as defined above;

each of m, n and o, equal or different from each other, is an integer higher than 1; and E is —(C$_6$H$_4$)—NH—(C=O)—(C$_6$H$_5$).

As will be apparent from the description of the process for the synthesis of co-polymer (P) below, co-polymer (P) is provided in a mixture comprising polymer (P) and a minor amount of its corresponding di-functional polymer, which complies with the following chemical formula:

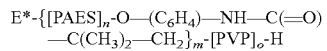

wherein [PAES], [PVP], n and o are as defined above and E* is group —O—(C$_6$H$_4$)—NH—C(=O)—C(CH$_3$)$_2$—CH$_2$-[PVP]$_o$-H.

Under step (I) of the process of the present invention, said polymer (PAES)$_{NN}$ can be prepared using suitable reactants known to the person skilled in the art.

For example, when polymer (P) comprises PPSU recurring units, polymer (PAES)$_{NN}$ suitable under step (I) can be prepared starting from RADEL® PPSU, commercially available from Solvay Specialty Polymers USA, L.L.C.

When polymer (P) comprises PES recurring units, polymer (PAES)$_{NN}$ can be prepared starting from VERADEL® PESU from Solvay Specialty Polymers USA, L.L.C.

When polymer (P) comprises PSU recurring units, polymer (PAES)$_{NN}$ can be prepared starting from UDEL® PSU from Solvay Specialty Polymers USA, L.L.C.

According to the preferred embodiment wherein polymer (P) comprises (PEES) recurring units, polymer (PAES)$_{NN}$ suitable under step (I) is commercially available from Solvay-Cytec Industries under the name KM-177.

Under step (II) of the process of the invention, a free radical polymerization reaction is performed, wherein said polymer (PAES)$_{NN}$ is reacted with a suitable unsaturated carboxylic acid or acid chloride, such as for example methacryloyl chloride, acryloyl chloride, acrylic acid, methacrylic acid and similar olefin containing acids, acid chlorides or their derivatives.

Preferably, after step (I) and before step (II), said (PAES)$_{NN}$ polymer is advantageously dissolved in a polar aprotic solvent, preferably selected from dimethylacetamide (DMAC), N-methyl pyrrolidone (NMP), N-butylpyrrolidinone (NBP), dimethylformamide (DMF), dimethyl sulfoxide (DMSO), sulfolane, chloroform,1,3-Dimethyl-2-imidazolidinone (DMI).

Preferably, step (II) is performed under heating, more preferably at a temperature from room temperature to 100° C.

Preferably, step (II) is performed in the presence of a polar aprotic solvent, as those listed above.

Advantageously, when step (II) is performed under the above mentioned conditions, mixture (M-P1) is obtained comprising a majority of said polymer $(PAES)_{NA}$ compared to said polymer $NA(PAES)_{NA}$.

Preferably, mixture (M-P1) comprises a ratio of said polymer $(PAES)_{NA}$ to said polymer $NA(PAES)_{NA}$ of at least 1.01:1, preferably of 1.5:1, preferably of 2:1.

Mixture (M-P1) is advantageously used as such under step (Ill) of the process of the invention, as the presence of said polymer $NA(PAES)_{NA}$ does not negatively affect the reactivity of the subsequent steps. However, if desired, the person skilled in the art can separate or remove said polymer $NA(PAES)_{NA}$ from mixture (M-P1) using separation or purification methods known in the art.

Preferably, said step (Ill) is performed in the presence of a polar aprotic solvent, as those listed above.

Preferably, under step (Ill), said $(PAES)_{NA}$ polymer is reacted with PVP in the presence of at least one radical initiator, more preferably selected from azo compounds such as azobisisobutyronitrile (AIBN), or peroxides, such as benzoyl peroxide or hydroperoxides.

Preferably, step (III) is performed under heating, more preferably at a temperature between 50° C. and 100° C.

According to a preferred embodiment, composition (C) according to the present invention comprises at least one polymer (P) as defined above, at least one pore-former and at least one medium (L).

According to this embodiment, composition (C) preferably comprises:
from 0.01 to 30 wt. % of at least one polymer (P);
from 1 to 10 wt. % of at least one pore-former; and
from 65 to 98.99 wt. % of at least one medium (L).

Preferably, said at least one pore-former is selected from PVP;
polyethyleneglycol, polyglycol monoesters and co-polymers of polyethyleneglycols with polypropyleneglycol, such as for example the polymers that are commercially available by BASF AG under the trade name Pluronic® F 68, F 88, F 108 and F 12; polysorbates, such as for example polyoxyethylenesorbitane monooleate, monolaurate or monopalmitate, which are for example marketed under the trade name Tween®.

Preferably, said at least one medium (L) is selected from water or polar aprotic solvents. More preferably, said polar organic solvent is selected in the group comprising: N,N-dimethylacetamide (DMAc), N,N-diethylacetamide, dimethylformamide (DMF), diethylformamide, NMP, DMI, DMSO, NPB and Rhodiasolv® Polarclean.

According to another preferred embodiment, composition (C) according to the present invention comprises at least one polymer (P) as defined above, at least one PVP polymer, at least one PAES polymer and at least one medium (L).

According to this embodiment, composition (C) preferably comprises:
at least one polymer (P) in an amount from 0.01 to 10 wt. %, more preferably from 0.5 to 8 wt. % and even more preferably from 0.9 to 8 wt. %, based on the total weight of said composition (C);
at least one pore-former in an amount from 1 to 10 wt. %, based on the total weight of said composition (C);
at least one PAES polymer in an amount from 1 to 35 wt. %, more preferably from 5 to 25 wt. % and even more preferably from 10 to 20 wt. % based on the total weight of said composition (C); and
at least one medium (L) in an amount from more than 60 to 97.99 wt. %, more preferably from 65 to 95 wt. % and even more preferably from 70 to 90 wt. % based on the total weight of said composition (C).

Preferably, said PAES polymer is selected in the group comprising, preferably consisting of, polyphenylsulfone (PPSU), polyethersulfone (PES), polyetherethersulfone (PEES) and polysulfone (PSU), as defined above.

Excellent results were obtained when said PEAS polymer was PSU or PES.

According to a preferred embodiment, composition (C) is free of plasticizing agents, i.e. either plasticizing agents are not added to composition (C) or they are present in an amount of less than 1 wt. %, more preferably less than 0.1 wt. % based on the total weight of said composition (C).

Membranes containing pores homogeneously distributed throughout their thickness are generally known as symmetric (or isotropic) membranes; membranes containing pores which are heterogeneously distributed throughout their thickness are generally known as asymmetric (or anisotropic) membranes.

Membrane (Q) may be either a symmetric membrane or an asymmetric membrane.

The asymmetric membrane (Q) typically comprises an outer layer containing pores having an average pore diameter smaller than the average pore diameter of the pores in one or more inner layers. Each of said layer(s) can be layer ($L_Q$) as defined above.

The porous membrane of the invention preferably has an average pore diameter lower than 100 nm, more preferably lower than 50 nm and even more preferably lower than 10 nm. According to a preferred embodiment, the membrane of the invention suitable for use for hemo-dialysis, has an average pore diameter lower than 8 nm. Membranes prepared for use other than hemo-dyalysis have an average pore diameter from 0.001 µm to 50 µm.

Suitable techniques for the determination of the average pore diameter in the porous membranes of the invention are described for instance in Handbook of Industrial Membrane Technology. Edited by PORTER, Mark C. Noyes Publications, 1990. p. 70-78. Pore size of the membrane may be estimated by several techniques including Scanning Electron Microscopy (SEM), and/or measurements of bubble point, gas flux, water flux, and molecular weight cut off.

The membrane (Q) typically has a gravimetric porosity comprised between 5% and 90% by volume, preferably between 10% and 85%, more preferably between 30% and 75%, based on the total volume of the membrane. Good results have been obtained for gravimetric porosity between 70 and 85% by volume.

Suitable techniques for the determination of the gravimetric porosity in membrane (Q) are described for instance by SMOLDERS, K., et al. Terminology for membrane distillation. *Desalination*. 1989, vol. 72, p. 249-262.

Membrane (Q) may be either a self-standing porous membrane comprising said layer ($L_Q$) as the only layer or a multi-layered membrane, preferably comprising said layer ($L_Q$) supported onto a substrate.

Said substrate layer may be partially or fully interpenetrated by said layer ($L_Q$).

Said substrate is preferably made of material(s) having a minimal influence on the selectivity of the porous membrane. The substrate layer preferably consists of non-woven materials, glass fibers and/or polymeric material such as for example polypropylene, polyethylene, polyethyleneterephthalate.

Membrane (Q) is manufactured according to conventional methods, such as phase-inversion methods.

Usually, for the manufacture of membrane (Q), a composition (C) is manufactured by a conventional method, processed into a film (F) and, optionally film (F), is further processed into a membrane (Q).

According to a first embodiment, film (F) and membrane (Q) are manufactured by means of a process occurring in the liquid phase [process (MP-1)], which typically comprises:
(i^) providing composition (C) as defined above;
(ii^) processing composition (C) provided in step (i^) thereby providing a film (F); and optionally,
(iii^) processing film (F) obtained in step (ii^) thereby providing membrane (Q).

Under step (i^), composition (C) is manufactured by any conventional techniques. For instance, medium (L) can be added to co-polymer (P) and, optionally, to polymer (PAES) and to any further ingredient, or, preferably, polymer (PAES) and, optionally, polymer (P) and any further ingredient are added to medium (L); alternatively, polymer (PAES) and, optionally, polymer (P), any further ingredient and medium (L) are simultaneously mixed.

Any suitable mixing equipment may be used. Preferably, the mixing equipment is selected to reduce the amount of air entrapped in composition (C) which may cause defects in the final membrane. Mixing is conveniently carried out in a sealed container, optionally kept under an inert atmosphere. Inert atmosphere, and more precisely nitrogen atmosphere has been found particularly advantageous for the manufacture of composition (C).

Under step (i^), the mixing time during stirring required to obtain a clear homogeneous composition (C) can vary widely depending upon the rate of dissolution of the components, the temperature, the efficiency of the mixing apparatus, the viscosity of composition (C) and the like.

Under step (ii^), composition (C) is typically processed in the liquid phase. Under step (ii^), composition (C) is typically processed by casting, thereby providing a film (F).

Casting generally involves solution casting, wherein typically a casting knife, a draw-down bar or a slot die is used to spread an even film of a liquid composition comprising a suitable medium (L) across a suitable support.

Under step (ii^), the temperature at which composition (C) is processed by casting may or may not be the same as the temperature at which composition (C) is mixed under stirring.

Different casting techniques are used depending on the final form of membrane (Q).

When membrane (Q) is a flat membrane, composition (C) is cast as a film (F) over a flat supporting substrate, typically a plate, a belt or a fabric, or another microporous supporting membrane, typically by means of a casting knife, a draw-down bar or a slot die.

According to a first embodiment of step (ii^), composition (C) is processed by casting onto a flat supporting substrate to provide a flat film (F).

According to a second embodiment of step (ii^), composition (C) is processed by casting to provide a tubular film (F).

According to a variant of this second embodiment of the invention, the tubular film (F) is manufactured using a spinneret.

The term "spinneret" is hereby understood to mean an annular nozzle comprising at least two concentric capillaries: a first outer capillary for the passage of composition (C) and a second inner one for the passage of a supporting fluid, generally referred to as "lumen". Optionally, an external outer capillary can be used to extrude a coating layer.

Hollow fibers and capillary membranes can be manufactured by a so-called "spinning process" according to this variant of the second embodiment of step (ii^). According to this variant, composition (C) is generally pumped through the spinneret; the lumen acts as support for the casting of the composition (C) and maintains the bore of the hollow fiber or capillary precursor open. The lumen can be a gas, or, preferably, a medium (NS) or a mixture of a medium (NS) with a medium (L). The selection of the lumen and its temperature depends on the required characteristics of the final membrane as they may have a significant effect on the size and distribution of the pores in the membrane.

At the exit of the spinneret, after a short residence time in air or in a controlled atmosphere, under step (iii^) of (MP-1), the hollow fiber or capillary precursor is precipitated, thereby providing a hollow fiber or capillary membrane (Q).

The supporting fluid forms the bore of the final hollow fiber or capillary membrane (Q).

Because of their larger diameter, tubular membranes are generally manufactured using a different process from the one employed for the production of hollow fiber membranes.

The temperature gradient between the film provided in any one of steps (ii^) and (iii^) of process (MP-1) and medium (NS) shall be selected by a person skilled in the art in such a way as to adjust the rate of precipitation of (PAES) polymer from composition (C).

Thus, a first variant of process (MP-1) comprises:
(i^*) providing composition (C) as defined above;
(ii^*) processing composition (C) provided in step (i^*) thereby providing a film; and optionally
(iii^*) contacting the film provided in step (ii^*) with a non-solvent medium [medium (NS)], thereby providing a membrane (Q).

A further variant of [process (MP-1)] comprises:
(i^**) providing composition (C) as defined above;
(ii^) processing composition (C) provided in step (i^) thereby providing a film; and optionally
(iii^) processing the film provided in step (ii^) by cooling thereby providing a porous membrane (Q).

Under step (ii^**), the film is typically processed at a temperature high enough to maintain composition (C) as a homogeneous solution.

Under step (ii^**), the film is typically processed at a temperature comprised between 60° C. and 250° C., preferably between 70° C. and 220°, more preferably between 80° C. and 200° C.

Under step (iii^), the film provided in step (ii^) is treated by cooling to a temperature below 100° C., preferably below 60° C., more preferably below 40° C., typically using any conventional techniques.

Under step (iii^**), cooling is typically carried out by contacting the film provided in step (ii) with a liquid medium [medium (L')].

Under step (iii^**), the medium (L') preferably comprises, and more preferably consists of, water.

Alternatively, under step (iii^), cooling is carried out by contacting the film provided in step (ii^) with air.

Under step (iii^**), either the medium (L') or air is typically maintained at a temperature below 100° C., preferably below 60° C., more preferably below 40° C.

A further variant of process (MP-1) comprises:
(i^***) providing composition (C) as defined above;
(ii^*) processing composition (C) provided in step (i^*) thereby providing a film (F); and optionally
(iii^*) processing film (F) provided in step (ii^*) by absorption of a non-solvent medium [medium (NS)] from a vapour phase thereby providing a porous membrane (Q).

Under step (iii^*), film (F) provided in step (ii^*) is preferably precipitated by absorption of water from a water vapour phase.

Under step (iii^*), film (F) provided in step (ii^*) is preferably precipitated under air, typically having a relative humidity higher than 10%, preferably higher than 50%.

A variant of [process (MP-1)] comprises:
(i^****) providing composition (C) as defined above;
(ii^**) processing composition (C) provided in step (i^**) thereby providing a film (F); and optionally
(iii^**) processing the film provided in step (ii^**) by evaporation of medium (L) thereby providing a porous membrane (Q).

Preferably, when medium (L) comprise more than one organic solvents, step (ii^**) comprises processing composition (C) to provide a film, which is then precipitated in step (iii^**) by evaporation of medium (L) at a temperature above the boiling point of the organic solvent having the lowest boiling point.

According to a preferred embodiment, step (ii^****) is performed by processing composition (C) with a high voltage electric field.

A process (MP-1) may consist in one or more of the variants described herein before.

Membrane (Q) obtainable by process (MP-1) may undergo additional post treatment steps, for instance rinsing and/or stretching and/or thermal treatment (annealing).

Membrane (Q) obtainable by the process (MP-1) is typically rinsed using a liquid medium miscible with the medium (L).

Membrane (Q) obtainable by (MP-1) may be advantageously stretched so as to increase its average porosity.

Depending on its final intended use, membrane (Q) can be flat, when flat membranes are required, or tubular in shape, when tubular or hollow fiber membranes are required.

When membrane (Q) is flat, its thickness is advantageously from about 10 to about 300 microns, more preferably from about 25 to about 150 microns.

When membrane (Q) is tubular, its outer diameter can be up to 10 mm.

When membrane (Q) has an outer diameter comprised between 0.5 mm and 3 mm, it is referred to as hollow fibers membrane. When membrane (Q) has a diameter of less than 0.5 mm, it is referred to as capillary membranes.

Films (F) and membranes (Q) according to the present invention can be used in several technical fields, notably for the filtration of liquid and/or gas phases and for reverse osmosis (as thin selective dense layer).

Thus, in one aspect, the present invention relates to the use of membrane (Q) for the filtration of liquid and/or gas phases comprising one or more solid contaminants.

In another aspect, the present invention relates to a method for filtering a liquid phase and/or a gas phase comprising one or more solid contaminants, said method comprising contacting said liquid phase and/or gas phase comprising one or more solid contaminants with membrane (Q) of the invention.

Liquid and gas phases comprising one or more solid contaminants are also referred to as "suspensions", i.e. heterogeneous mixtures comprising at least one solid particle (the contaminant) dispersed into a continuous phase (or "dispersion medium", which is in the form of liquid or gas).

Said at least one solid contaminant preferably comprises microorganisms, preferably selected from the group consisting of bacteria such as *Staphylococcus aureus* and *Pseudomonas aeruginosa*, algae, fungi, protozoa and viruses.

Membrane (Q) can be used for filtrating biologic solution (e.g. bioburden, virus, other large molecules) and/or buffer solutions (e.g. solutions that may contain small amount of solvents like DMSO or other polar aprotic solvents).

In one embodiment, two or more porous membranes (Q) can be used in series for the filtration of a liquid and/or gas phase. Advantageously, a first filtration step is performed by contacting liquid and/or gas phases comprising one or more solid contaminants with a membrane (Q) according to the present invention having an average pore diameter higher than 5 μm, more preferably from 5 to 50 μm; and a second filtration step is performed after said first filtration step, by contacting the same liquid and/or gas phase with a membrane (Q) having an average pore diameter of from 0.001 to 5 μm.

Alternatively, at least one membrane (Q) is used in series with at least one porous membrane obtained from a composition different composition (C) according to the present invention.

According a specific and further embodiment of the invention, membranes (Q) in the form of tubular or hollow fibers and having average pore diameter of from 0.001 to 5 μm are used within an extracorporeal blood circuit or a dialysis filter to purify biological fluids, namely blood. It has indeed been observed that, membranes (Q) according to the present invention are antithrombogenic; in particular, it has been observed that membranes (Q) comprising co-polymer (P) of the present invention have a antithrombogenic effect.

As used herein, the term "antithrombogenic" means that the rate at which thrombosis occurs when whole blood is contacted with a membrane (Q) is lower than that when whole blood is contacted with a membrane prepared starting from a composition free from co-polymer (P). It is well known in the art, for example from US 2015/0008179 (INTERFACE BIOLOGICS INC.), that when blood is transported to and from the body of patients receiving haemodialysis, anticoagulants such as heparin are typically added to prevent clotting or thrombosis. However, if on the one hand the use of heparin is advantageous, it can be complicated by allergic reactions and bleeding and, in addition, it is contraindicated in patients taking certain medications.

Thus, in a further aspect, the present invention relates to the use of a membrane (Q) in the form of hollow fiber having an average pore diameter of from 1 nm to 16 nm as component in an extracorporeal blood circuit or in a dialysis filter.

In a further aspect, the present invention relates to a method for treating a subject suffering from impaired kidney function, the method comprising subjecting a patient to a procedure selected from haemodialysis, hemofiltration, hemoconcentration or hemodiafiltration, said procedure being carried out with a dialysis filter comprising at least one membrane (Q) in the form of tubular or hollow fiber having an average pore diameter of from 1 nm to 16 nm.

In a further aspect, the present invention relates to a method for purifying a blood product, such as whole blood, plasma, fractionated blood component or mixtures thereof, wherein the method includes dialyzing said blood product across at least one hollow fiber membrane having an average pore diameter of from 0.001 to 5 µm and comprising at least one layer ($L_O$) as defined above.

Should the disclosure of any patents, patent applications, and publications which are incorporated herein by reference conflict with the description of the present application to the extent that it may render a term unclear, the present description shall take precedence.

The invention will be herein after illustrated in greater detail by means of the Examples contained in the following Experimental Section; the Examples are merely illustrative and are by no means to be interpreted as limitative of the scope of the invention.

Experimental Section

Materials

The following were obtained from Sigma-Aldrich, U.S.A.:

dimethyl acetamide (DMAc), chlorobenzene (MCB), azobisisobutyronitrile (AIBN), vinyl pyrrolidone monomer, methacryloyl chloride, tributyl amine, Polyvinyl pyrrolidone (PVP) K 90 and isopropyl alcohol (IPA).

Amine-terminated PEES polymer (KM-177), VERADEL® 3000 MP polyethersulfone (PESU) and UDEL®3500 LCD MB3 (PSU) were obtained from Solvay Specialty Polymers U.S.A., LLC.

Methods

GPC—Molecular weight (Mn, Mw)

Viscotek GPC Max (Autosampler, pump, and degasser) with a TDA302 triple detector array comprised of RALS (Right Angle Light Scattering), RI and Viscosity detectors was used.

Samples were run in NMP with 0.2 w/w % LiBr at 65° C. at 1.0 mL/min through a set of 3 columns: a guard column (CLM1019—with a 20 k Da exclusion limit), a high Mw column (CLM1013 exclusion of 10 MM Daltons relative to Poly Styrene) and a low Mw column (CLM1011—exclusion limit of 20 k Daltons relative to PS).

Calibration was done with a single, mono-disperse polystyrene standard of ~100 k Da.

Light Scattering, RI, and Viscosity detectors were calibrated based on a set of input data supplied with the standards.

Samples were prepared as ~2 mg/mL in NMP/LiBr.

Viscotek's OMNISec v4.6.1 Software was used for data analysis.

Thermal Gravimetric Analysis (TGA)

TGA experiments were carried out using a TA Instrument TGA Q500. TGA measurements were obtained by heating the sample at a heating rate of 10° C./min from 20° C. to 800° C. under nitrogen.

$^1$H NMR $^1$H NMR spectra were measured using a 400 MHz Bruker spectrometer with TCE as the deuterated solvent. All spectra are reference to residual proton in the solvent.

DSC

DSC was used to determine glass transition temperatures ($T_g$). DSC experiments were carried out using a TA Instrument Q100. DSC curves were recorded by heating, cooling, re-heating, and then re-cooling the sample between 25° C. and 320° C. at a heating and cooling rate of 20° C./min. All DSC measurements were taken under a nitrogen purge. The reported $T_g$ values were provided using the second heat curve unless otherwise noted.

Contact Angle

The static contact angle towards water was evaluated at 25° C. by using the DSA10 instrument (from Krüss GmbH, Germany) according to ASTM D5725-99.

The measures were taken at the up side (interface with air) of the membranes and dense films. The values are average of at least 6 measurements.

Gravimetric Porosity

Gravimetric porosity of the membrane was defined as the volume of the pores divided by the total volume of the membrane.

Membrane porosity (ε) was determined according to the gravimetric method detailed below.

Perfectly dry membrane pieces were weighed and impregnated in isopropyl alcohol (IPA) for 24 h. After this time, the excess of the liquid was removed with tissue paper, and membranes weight was measured again. The porosities were measured using IPA (isopropyl alcohol) as wetting fluid according to the procedure described in Appendix of Desalination, 72 (1989) 249-262.

$$\varepsilon = \frac{\frac{(\text{Wet} - \text{Dry})}{\rho_{liquid}}}{\frac{(\text{Wet} - \text{Dry})}{\rho_{liquid}} - \frac{\text{Dry}}{\rho_{polymer}}}$$

where

'Wet' was the weight of the wetted membrane,

'Dry' was the weight of dry membrane, $\rho_{polymer}$ was the density of PSU (1.30 g/cm$^3$) and $\rho_{liquid}$ was the density of IPA (0.78 g/cm$^3$).

Tensile Measurements

Mechanical properties on flat sheet porous membranes were assessed at room temperature (23° C.) following ASTM D 638 standard procedure (type V, grip distance=25.4 mm, initial length Lo=21.5 mm). Velocity was between 1 and 50 mm/min. The flat sheet porous membranes stored in water were took out from the container boxes and immediately tested Water Uptake Water uptake tests were performed according to ASTM D570 ("Standard test method for absorption of plastics") on dense non porous films. Specimens (approximately 2×3 cm$^2$ each) were dried in a vacuum oven for 24 h at 105° C., then cooled in a desiccator and immediately weighed to the nearest 0.001 g. Then they were placed in a container of distilled water maintained at a temperature of 23±1° C. After 48 h of immersion, they were removed from the water one at a time, all surface water wiped off with a dry cloth, and weighed to the nearest 0.001 g immediately. Quoted values are the averages of at least 6 items for each polymer type.

Synthesis

Step (a): Synthesis of the methacryloylated polyetherethersulfone

The reaction took place in a glass reactor vessel (1 L) fitted with an overhead stirrer, nitrogen inlet and an overhead distillation set-up. The KM-177 (600 g) was dried overnight at 110° C. under vacuum and then charged to the reactor. Next, dimethylacetamide (900 g) was added and the polymer was dissolved. Tributyl amine (132 g) and chlorobenzene (300 g) were added to the polymer solution.

The reaction mixture was heated from room temperature to 170° C. using a 1° C./min heating ramp, such that most of the chlorobenzene was distilled off. Then heating was lowered such that the internal temperature reached 60° C.

and the methacryloyl chloride was added drop-wise over a period of 30 minutes. The reaction was allowed to proceed at 60° C. for 12 hours. Afterwards, benzoyl chloride (10.11 g) was added and the reaction was carried out for additional four hours.

After the reaction was complete, the reaction mixture was coagulated into methanol (3 L) and washed with hot water and then dried in a vacuum oven at 110° C. overnight.
Characterization:

GPC: $M_n$=21035 g/mol, $M_w$=10158 g/mol, PDI=2.07

TGA: the onset of thermal degradation was observed at 500° C.

DSC: a thermal transition corresponding to the $T_g$ was observed at 199° C.

$^1$H-NMR (d-TCE solvent): the presence of methacryloyl group was confirmed by the appearance of a singlet 2.08 ppm of the methyl group and two singlets at 5.5 and 5.8 ppm of the olefinic protons which were not present in the polymer before the reaction.

Step (b): Co-polymerization of the methacryloylated polyetherethersulfone

The reaction took place in a glass reactor vessel (1 L) fitted with an overhead stirrer, nitrogen inlet and an overhead distillation set-up. The methacrylated polyethethersulfone (PEES) (150 g) obtained in Step (a) was dried overnight at 110° C. under vacuum and then charged to the reactor. Then, dimethylacetamide (1500 g) was added and the polymer was dissolved. To the polymer solution, vinyl pyrrolidone (200.25 g) was added and the solution was de-gassed by purging N2 for 30 minutes at room temperature.

Then AIBN was added to the reaction mixture and the reaction temperature was increased to 60° C. for 2 hours, after which the reaction temperature was increased the temperature to 75° C. for 24 hours.

The reaction mixture was then coagulated into water and the coagulated material washed with 300 g of boiling water for 1 hour. This was repeated for five times, each using fresh water wash to ensure that any free PVP polymer was washed out. After the fifth water wash, the polymer was dried under vacuum at 100° C. overnight.
Characterization:

Light scattering GPC: $M_n$=373042 g/mol, $M_w$=1321000 g/mol, PDI=3.54

TGA: The TGA showed two distinct thermal degradation temperatures: the onset of thermal degradation at 379° C. indicative of the PVP thermal degradation and the other at 520° C. indicative of PEES degradation.

DSC: a single $T_g$ was observed at 207° C.

$^1$H NMR: There was complete disappearance of the methacryloyl olefinic protons and presence of broad peaks in the aliphatic region, characteristic of polyvinyl pyrrolidone were seen.

Contact Angle: The contact angle of a film of the polymer cast was lower than typical PEES polymer at 66° indicating a more hydrophilic surface as compared to unmodified PEES polymer.

General Procedure for the Manufacture of Solutions of Co-Polymer (P) for Porous Membrane or Dense Film Manufacture Solutions were prepared by mixing in a glass bottle by magnetic stirring the selected polymers (PSU or PESU) and/or co-polymer (P) as obtained at the end of Step (b) described above. DMAc and, optionally, the pore-forming agent (PVP K90) were added and stirring was performed for a time ranging from 30 minutes to 6 hours in a temperature range from 25° C. to 80° C.

Solutions were prepared having the composition provided in Table 1 below.

TABLE 1

| Sample No. | PSU wt. % | PESU wt. % | co-polymer (P) wt. % | DMAc wt. % |
|---|---|---|---|---|
| 1 | 0 | — | 20 | 80 |
| 2(*) | 20 | — | 0 | 80 |
| 3 | 19 | — | 1 | 80 |
| 4 | 18 | — | 2 | 80 |
| 5 | — | 19 | 1 | 80 |
| 6(*) | — | 20 | 0 | 80 |

(*)comparison

Preparation of Dense Films

Flat sheet films were prepared by filming the polymeric solutions obtained following the procedure disclosed above, over a suitable smooth glass support by means of an automatized casting knife, at 40° C. The knife gap was set at 500 μm. After casting, the solvent was left to evaporate in a vacuum oven at 130° C. for several hours.

Dense films were prepared starting from Samples No. 1, 5 and 6(*) and their mechanical properties of the dense films were evaluated. Results are reported in the following Table 2:

TABLE 2

| Sample No. | PESU wt. % | Polymer (P) wt. % | DMAc wt. % | Modulus (MPa) | Stress @ break (MPa) | Strain @ break (%) |
|---|---|---|---|---|---|---|
| 1 | — | 20 | 80 | 2251 | 4.39 | 5.5 |
| 5 | 19 | 1 | 80 | 1992 | 14 | 31.5 |
| 6(*) | 20 | 0 | 80 | 2122 | 9.7 | 8.4 |

(*) comparison

Preparation of Porous Membranes

Flat sheet porous membranes were prepared by filming solutions over a suitable smooth glass support by means of an automatized casting knife.

Membrane casting was performed by keeping the dope solutions, the casting knife and the support temperatures at 25° C., so as to prevent premature precipitation of the polymer. The knife gap was set to 250 μm.

After casting, films of porous membranes were immediately immersed in a coagulation bath in order to induce phase inversion. The coagulation bath consisted of pure de-ionized water or a mix water/DMAC 50/50 v/v. After coagulation, the membranes were washed several times in pure water during the following days to remove residual solvent traces. The membranes were stored (wet) in water.

Porous membranes were prepared starting from solution sample No. 1 and from solution sample No. 4, to which PVP K90 was added in the amounts detailed in the following Table 3. The coagulation bath and the properties of the membranes are also detailed in Table 3:

TABLE 3

| Sample No. | PSU wt. % | Polymer (P) wt. % | PVP K90 | DMAc wt. % | Coagulation bath:ratio H2O/DMAc | Contact angle (°) | Porosity (%) |
|---|---|---|---|---|---|---|---|
| 1 | 0 | 20 | 0 | 80 | 100/0 | — | 87 |
| 4-a | 18 | 2 | 2 | 78 | 100/0 | 84 | 85 |

TABLE 3-continued

| Sample No. | PSU wt. % | Polymer (P) wt. % | PVP K90 | DMAc wt. % | Coagulation bath:ratio H2O/DMAc | Contact angle (°) | Porosity (%) |
|---|---|---|---|---|---|---|---|
| 4-b | 18 | 2 | 2 | 78 | 50/50 | 68 | 80 |
| 4-c | 18 | 2 | 5 | 75 | 100/0 | 86 | 85 |
| 4-d | 18 | 2 | 5 | 75 | 50/50 | 56 | 81 |

The covalent link between the PVP and the PESU or PSU polymer was demonstrated by performing an NMR analysis on the dense film and porous membranes as showed in the following Table 4:

TABLE 4

| Sample | PVP content as determined by NMR Method | |
|---|---|---|
| Dense film from Sample 1 | 20% | No washing |
| Porous membrane from Sample 1 | 20% | Washing in the coagulation bath |
| Porous membrane from Sample 1 | 20% | Washing with water at 90° C. (twice - 4 hours each) |

Blood Coagulation Tests (Determination of the Unactivated Partial Thromboplastin Time-uPTT)

Partial thromboplastin time (uPTT) of blood plasma contacted with non-porous dense films was evaluated (in duplicate) according to ISO 10993-4:2017 [Hemocompatibility test-Biological evaluation of medical devices—Part 4: Selection of tests for interactions with blood]. The test was performed using plasma blood from patients chosen randomly and not treated with anticoagulant therapy.

12 cm$^2$ (6+6 cm$^2$) specimens of non-porous dense films were immersed in 2 ml of plasma in order to reach a surface/volume ratio of 6 cm2/ml and incubated for 30 minutes at a temperature of 37° C.±1° C. in dynamic condition (stirrer).

Haematic determinations were conducted on both control plasma, which did not come into contact with the test item, and test plasma, which came into contact with test item. The clotting time values was calculated as percent of the negative control using the following equation:

$$D=[(T-C)/T]\times 100$$

where:
D=Difference between Treated and Control (%)
T=Average of uPTT time values of treated plasma, i.e plasma exposed to the item (in seconds; repeated twice)
C=Average of uPTT time values of control plasma (in seconds; repeated twice).

The results are reported in Table 5 below.

Platelet Aggregation Tests

A biological evaluation was carried out aimed to obtain the necessary data to evaluate if samples interact with whole blood inducing platelet aggregation.

Test was accomplished according to to ISO 10993-4: 2017. The hemocompatibility test was performed using blood from donors chosen randomly and not treated with anticoagulant therapy.

12 cm2 (6+6 cm$^2$) of the test item was immersed in 2 ml of blood in order to reach a surface/volume ratio of 6 cm2/ml and incubated for 30 minutes at a temperature of 37° C.±1° C. in dynamic condition (stirrer).

Control haematic determinations were conducted on the remaining part of the portions of lithium-heparin blood that did not come in contact with the test item.

The platelet aggregation test assesses the ability of platelets to adhere to one another. Platelets are activated by the activator TRAP-6 (Thrombin Receptor Activating Peptide 6) and through two electrodes submerged into the blood. The test measures the electric impedance variation that occur when platelets aggregate.

Results are expressed as speed of aggregation over time and the area under the curve (AUC) was measured (two independent determinations performed in the same tube and contemporary). If the contact with a test item causes platelet aggregation, a reduction of this parameter is detected.

Result "Area under curve" (AUC) is expressed as AU/min (absorbance units) and is the mean between two independent and contemporary determinations executed on the same test tube.

Values are expressed as:

$$D=[(T-C)/T]\times 100$$

where:
D=Difference between Treated and Control (%)
T=treated specimen (AUC, blood exposed to the sample)
C=control AUC (AUC, control blood not in contact with the sample)

A positive values indicated the absence of aggregation at all (i.e.: better than the control blood not exposed to the specimen).

The results are reported in Table 5 below.

TABLE 5

| Ingredients | Wt. Ratio | Platelet aggregation (%) | Coagulation μPTT (%) |
|---|---|---|---|
| PSU/polymer P | 90/10 | +12 | −8.32 |
| PSU/PVP (*) | 96/4 | +2.7 | −5.25 |
| PESU/PVP (*) | 96/4 | −12.5 | −11.90 |

(*) comparison

The above results showed that the addition of polymer P reduced the coagulation propensity of blood, making the composition of the invention better than the two control samples for the preparation of membrane for hemodialysis.

The invention claimed is:

1. A co-polymer (P) comprising:
   a first segment comprising poly(aryl ether sulfone) (PAES) recurring units, and
   a second segment comprising poly(vinyl pyrrolidone) (PVP) recurring units,
   wherein said first segment and said second segment are linked together via a group of formula —O-Ph-NH—C(=O)—C(CH$_3$)$_2$—CH$_2$—.

2. The co-polymer (P) according to claim 1, wherein said co-polymer (P) comprises more than 5 wt. % of said PVP recurring units, based on the total weight of the co-polymer (P).

3. The co-polymer (P) according to claim 1, wherein said PVP recurring units comply with the following formula (I):

(I)

wherein o is an integer higher than 1.

4. The co-polymer (P) according to claim 1, wherein said PAES recurring units comprise at least 50 mol. % of recurring units ($R_{PAES}$) of formula (K):

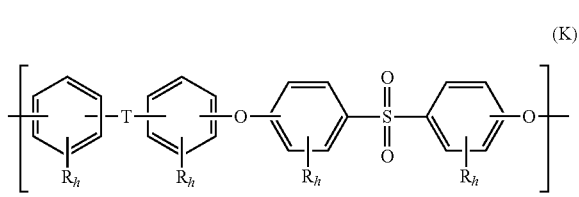

where
each R, equal to or different from each other, is selected from the group consisting of a halogen, an alkyl, an alkenyl, an alkynyl, an aryl, an ether, a thioether, a carboxylic acid, an ester, an amide, an imide, an alkali or alkaline earth metal sulfonate, an alkyl sulfonate, an alkali or alkaline earth metal phosphonate, an alkyl phosphonate, an amine, and a quaternary ammonium;
each h, equal to or different from each other, is an integer ranging from 0 to 4; and
T is selected from the group consisting of a bond, a sulfone group [—S(=O)$_2$-], and a group —C($R_j$)($R_k$)—, where $R_j$ and $R_k$, equal to or different from each other, are selected from a hydrogen, a halogen, an alkyl, an alkenyl, an alkynyl, an ether, a thioether, a carboxylic acid, an ester, an amide, an imide, an alkali or alkaline earth metal sulfonate, an alkyl sulfonate, an alkali or alkaline earth metal phosphonate, an alkyl phosphonate, an amine, and a quaternary ammonium, $R_j$ and $R_k$ are preferably methyl groups.

5. The co-polymer (P) according to claim 1, wherein said PAES recurring units are selected from the group consisting of:
polysulfone (PSU) recurring units comprising at least 50 mol. % of recurring units of formula (K'-C):

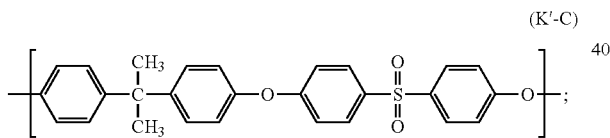

polyphenylsulfone (PPSU) recurring units comprising more than 50 mol. % of recurring units of formula (K'-A):

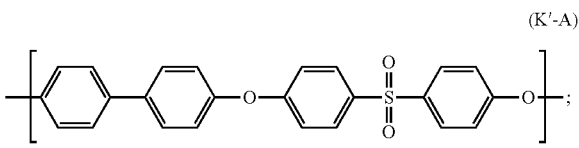

polyethersulfone (PES) recurring units comprising at least 50 mol. % of recurring units of formula (K'-B):

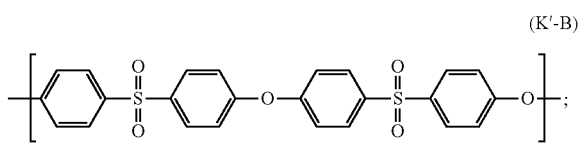

and
poly(ether ether sulfone) (PEES) recurring units comprising at least 50 mol. % of recurring units of formula (K'-D):

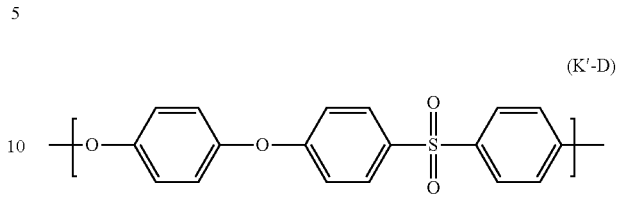

and
optionally recurring units of formula (K'-Db):

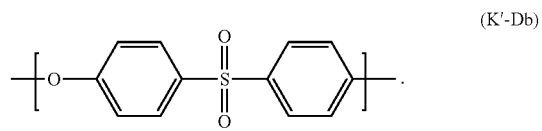

6. A process for the synthesis of the co-polymer (P) according to claim 1, said process comprising the following steps:
(I) providing a poly(aryl ether sulfone) polymer (PAES)$_{NN}$ having two chain ends, wherein both chain ends comprise an amine group;
(II) reacting said polymer (PAES)$_{NN}$ with methacryloyl chloride thus providing a mixture (M-P1) comprising mono-methacrylated PAES polymer (PAES)$_{NA}$ and di-methacrylated PAES polymer $_{NA}$(PAES)$_{NA}$; and)
reacting said mixture (M-P1) obtained in step (II) with vinyl pyrrolidone monomer, thus providing a mixture comprising the co-polymer (P).

7. The process according to claim 6, wherein said step (II) is performed
by reacting said poly(aryl ether sulfone) polymer (PAES)$_{NN}$ with an unsaturated acid or acid chloride; and/or
under heating; and/or
in the presence of a polar aprotic solvent.

8. The process according to claim 6, wherein said mixture (M-P1) comprises a majority of said mono-methacrylated polymer (PAES)$_{NA}$ compared to said di-methacrylated polymer $_{NA}$(PAES)$_{NA}$, with a ratio of said mono-methacrylated polymer (PAES)$_{NA}$ to said di-methacrylated polymer $_{NA}$(PAES)$_{NA}$ of at least 1.01:1.

9. The process according to claim 6, wherein said step (III) is performed
in the presence of a polar aprotic solvent; and/or
in the presence of at least one radical initiator; and/or
under heating.

10. A composition (C) comprising:
the at least one co-polymer (P) of claim 1,
at least one pore-former, and
at least one medium (L).

11. The composition (C) according to claim 10, said composition (C) further comprising at least one poly(aryl ether sulfone) (PAES) polymer.

12. A membrane (Q) comprising at least one porous layer ($L_Q$), said layer ($L_Q$) being obtained from the composition (C) according to claim 10.

13. A method for the extracorporeal treatment of a patient's blood, said method comprising cleansing the blood via removal of uremic retention products by the use of at least one membrane (Q) according to claim 12 which is semi-permeable.

14. A method for treating a subject suffering from impaired kidney function, the method comprising subjecting a patient to a procedure selected from the group consisting of haemodialysis, hemofiltration, hemoconcentration and hemodiafiltration, said procedure being carried out with a dialysis filter comprising the at least one membrane (Q) according to claim 12, said membrane (Q) being in the form of tubular or hollow fiber having an average pore diameter of from 1 nm to 16 nm.

15. A method for purifying a blood product, wherein the method includes dialyzing said blood product across the at least one membrane (Q) according to claim 12, said membrane (Q) being in the form of hollow fiber having an average pore diameter of from 0.001 to 5 μm.

16. The composition (C) according to claim 10, comprising:
   the at least one co-polymer (P) in an amount from 0.01 to 30 wt. %;
   the at least one pore-former in an amount from 1 to 10 wt. %; and
   the at least one medium (L) in an amount higher than 60 wt. %,
   the amounts being based on the total weight of said composition (C).

17. The membrane (Q) according to claim 12, having an average pore diameter of from 0.001 to 50 μm.

18. The membrane (Q) according to claim 12, having an average pore diameter lower than 100 nm.

19. The co-polymer (P) according to claim 1, wherein said co-polymer (P) has a weight average molecular weight ($M_w$) from 50 000 g/mol to 2 000 000 g/mol (as determined by GPC).

* * * * *